United States Patent [19]

Stoner et al.

[11] 4,202,740

[45] May 13, 1980

[54] APPARATUS AND METHOD FOR DISINFECTING OBJECTS

[75] Inventors: Glenn E. Stoner; George L. Cahen, Jr., both of Charlottesville, Va.

[73] Assignee: Research Corporation, New York, N.Y.

[21] Appl. No.: 875,513

[22] Filed: Feb. 6, 1978

[51] Int. Cl.$^2$ ............................................. A61L 1/00
[52] U.S. Cl. ................................. 204/130; 204/1 R; 204/149; 204/268; 204/271; 204/285; 204/DIG. 6; 422/22
[58] Field of Search ............... 204/1 R, 149, 268, 270, 204/271, 287, 285, 254, 130, 191, 98, 128, DIG. 6; 426/237, 335; 422/22

[56] References Cited

U.S. PATENT DOCUMENTS

| 647,603 | 4/1900 | Kinne | 422/22 X |
|---|---|---|---|
| 909,831 | 1/1909 | Strecker-Aufermann | 204/268 X |
| 1,937,536 | 12/1933 | Steerup | 422/22 |
| 2,121,875 | 6/1938 | Kruse et al. | 204/271 X |
| 2,141,644 | 12/1938 | Eddison | 204/130 X |
| 2,485,660 | 10/1949 | Robertson | 422/22 X |
| 2,655,473 | 10/1953 | Lowenheim | 204/268 X |
| 2,739,112 | 3/1956 | Ferguson | 204/268 X |
| 3,522,167 | 7/1970 | Allen | 422/22 X |
| 3,784,453 | 1/1974 | Dworkin et al. | 204/271 X |

*Primary Examiner*—Arthur C. Prescott
*Attorney, Agent, or Firm*—Oblon, Fisher, Spivak, McClelland & Maier

[57] ABSTRACT

An apparatus for electrolytically disinfecting an object which comprises
  an electrolytic cell containing at least one pair of electrodes, said electrodes being positioned within said cell such that when said cell receives an electrolyte containing solution therein, said electrodes will be at least partially immersed in said solution,
  an electrically conductive substrate having means for holding said object to be disinfected, said electrically conductive substrate being of sufficient size so as to be capable of being immersed into the solution, when said cell receives said solution, between said electrodes, and wherein said substrate functions as a bipolar electrode when a potential is impressed across said electrodes, and wherein said holding means is capable of holding the object to be disinfected completely submerged in said solution, and between said electrodes.

26 Claims, 7 Drawing Figures

APPARATUS AND METHOD FOR DISINFECTING OBJECTS

BACKGROUND OF THE INVENTION

1. Field of the Invention

The present invention relates to methods and apparatus for electrolytic disinfecting of objects in electrolyte containing solutions. More particularly, the present invention relates to methods and apparatus for electrolytic disinfection of such objects as contact lenses.

2. Description of the Prior Art

The general technique of purifying water or aqueous solutions of pathogens by subjecting the water or aqueous solution to a current in an electrolysis cell between at least one pair of electrodes is well known. In Stoner, U.S. Pat. No. 3,725,226, there is disclosed a technique in which water containing pathogenic microorganisms, such as bacteria, viruses, disease flukes, protozoa or the like, is subjected to an alternating potential applied across at least one pair of electrodes immersed in an aqueous solution, thereby passing each electrode through alternate cathodic and anodic phases. The peak voltage during the anodic phase is less than the voltage at which vigorous electrolytic oxygen is generated, and the peak voltage during the cathodic phase is greater than the voltage at which hydrogen is generated. By impressing an alternating current across the electrodes, not only are the pathogenic microorganisms in solution deactivated, but also the electrodes are defouled of deactivated micoorganisms which might accumulate on the electrodes during the anodic phase.

Shaffer, in U.S. Pat. No. 3,923,629, discloses an electrolytic technique for water purification in which a water solution to be purified is passed into a cell such that the fluid passes through permeable electrode layers in the cell. An alternating current having a current potential ranging from about 0.1 to about 20 volts and a frequency ranging from 0.1 to 10 cps is impressed across the electrodes in the cell so that as the fluid passes through the cell it passes through zones containing pairs of electrodes across which is impressed the alternating current.

Yet another prior art technique for purifying water is described by Teshima et al in U.S. Pat. No. 3,888,756. In this method water containing such contaminants as metallic ions, cyahides, silica, organic ions or the like, flows through an electrolytic cell. The cell is filled with a fluidized medium of particles of a conductive material such as graphite, and particles of a non-conductive material, such as glass balls, plastic balls or the like. As the impure water flows through the cell, a DC current is impressed across the electrodes. Each of the conductive particles in the fluidized bed functions as a small electrode in the bath thereby facilitating the removal of the impurities within the aqueous solution. While all of the above discussed techniques are effective for the removal and deactivation of contaminants in aqueous solutions, none is entirely effective for all objects immersed within the aqueous solutions in the electrolytic cells.

While electrolytic techniques for disinfection are known where water, or an electrolyte containing media is intended to be disinfected, problems have occurred when it was attempted to disinfect solid objects of irregular contours by the same technique. Theoretically, if a solid object were placed in an aqueous medium between two electrodes and subjected to an alternating potential as discussed in the above referenced Stoner patent, the object should be disinfected. In practice, however, it was found that where the object is of irregular contours, the object itself masks the current so that contaminated areas of aqueous medium in the shadows of the object will not be disinfected.

In the past, objects fabricated from non-conductive materials such as contact lenses, false teeth, beauty objects and the like, have been disinfected by either chemical treatment or by being subjected to hot water. However, for some objects such as soft contact lenses, heat accelerates the degradation of the lens material. Further, the use of chemical disinfecting agents for contact lenses is not permitted in some countries. Moreover, the conventional disinfection techniques have the disadvantages that considerable time is required to disinfect the object to be sterilized and in many instances hazardous chemicals must be used to disinfect various objects.

An electrolytic technique for disinfection of solid objects such as contact lenses, would be quite desirable to overcome the disadvantages of chemical or heat treatment that are now commonly used. However, electrolytic techniques are hindered by the requirement that small objects such as contact lenses must be held by larger objects such as lens containers which enhance the masking problem discussed above. If the chamber within the holding container is wired to the electrodes, when the container is opened, contamination on the outer walls of the container could get onto the fingers and subsequently onto the lenses when they are removed from the container. Thus, present FDA regulations require that any contact lens disinfection system must provide for disinfection of the total lens container as well as the lenses.

Brendlinger et al, U.S. Pat. No. 3,926,767, disclose an electrolytic treating apparatus designed for the pickling of metal strips of uniform dimensions. The continuous metal strip is fed into an elongated container which contains an aqueous electrolyte medium, preferably also containing an odd number of electrode pairs. As the metal strip passes through the container, it passes between the electrodes of each pair of electrodes and is subjected to electrolyzing treatment under extremely high currents which pickles the metal strip. In this system, the passage of current from one electrode to the metal strip via the intervening electrolyte solution and then from the metal strip through the intervening electrolyte solution to the other electrode is known as bipolar electrolyzing, which is a quite different process from disinfection.

A need, therefore, continues to exist for a method and apparatus by which various objects, particularly electrically non-conductive objects, can be rapidly and simply disinfected.

SUMMARY OF THE INVENTION

Accordingly, one object of the present invention is to provide a method by which objects, particularly non-conductive objects, can be quickly and conveniently disinfected.

Another object of the present invention is to provide an apparatus containing an aqueous electrolyte and into which an object can be immersed for disinfection.

Briefly, these objects and other objects of the present invention as hereinafter will become more readily apparent have now been attained by providing an electrolytic cell containing at least one pair of electrodes, said electrodes being positioned within said cell such that when said cell receives an electrolyte containing solution therein, said electrodes will be at least partially immersed in said solution, and an electrically conductive substrate having means for holding the object to be disinfected, said electrically conductive substrate being of sufficient size so as to be capable of being immersed into the solution, when said cell receives said solution, between said electrodes, and wherein said substrate functions as a bipolar electrode when a potential is impressed across said electrodes, and wherein said holding means is capable of holding the object to be disinfected completely submerged in said solution, and between said electrodes.

Objects are disinfected using this apparatus by holding said object by an electrically conductive substrate, immersing the combination of said object and said electrically conductive substrate in an electrolyte solution within an electrolytic cell, wherein said cell contains at least one pair of electrodes, and impressing an alternating potential across the pair of electrodes.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
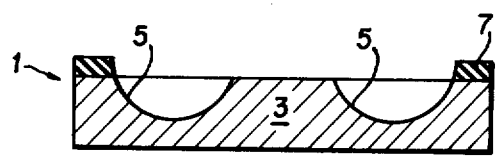
FIG. 1 is a lateral view of the female portion of a contact lens holder.

According to the present invention, an object to be disinfected, or in some instances sterilized, is immersed into an electrolytic solution, preferably an aqueous electrolyte solution, and a potential is impressed across the electrodes. This technique of disinfecting pathogens in an aqueous solution is fully described in the Stoner U.S. Pat. No. 3,725,226, herein incorporated by reference. According to that method, an alternating potential is impressed across the electrodes such that each electrode intermittently passes through cathodic and anodic phases. Generally, the magnitude of the potential should not exceed about ±5 volts, nor be less than about 200 m.v. During the anodic phase, micoorganisms present in the solution will be deactivated, presumably by yielding an electron to the electrode or by oxidation caused by an electrode produced intermediate. During the cathodic phase of the electrode, all protein and other organic matter coating the electrode as a result of anodic oxidation will be defouled from the electrode. Any waveform of alternating potential can be employed including triangular, sinusoidal, square wave and like patterns as described in the Stoner patent. Normally, the frequency of current used ranges from 0.1 to 10 cycles per second. The current density employed can range from one to 20 milliamps/cm$^2$, preferably one to five milliamps/cm$^2$.

In the present invention, an electrically conductive substrate is immersed in the electrolyte solution between the electrodes. When a potential is impressed across the electrodes, the electrically conductive substrate is activated and functions as a bipolar electrode. Each side of the electrically conductive substrate facing a principal electrode takes a partial charge opposite the charge on the electrode faced. Thus, the cell acts as if two separate cells in series are present.

The electrically conductive substrate is associated with means for holding an object to be disinfected. The associated holding means may be as simple as a hook or clamps for holding the object, or it can be more complex and specifically adapted to hold specific objects. For instance, the holding means may be in the form of a container. In this instance, the electrically conductive substrate may be in electrolytic contact with the interior of the container. The container might be equipped with a further holder whereby the container can be positioned within the electrolytic cell. One or more of the walls of the container itself may be formed from an electrically conductive material.

The size of the electrolytic cell should be sufficient such that the object being disinfected is entirely submerged within the electrolytic solution. Preferably, the holding means itself is also entirely submerged in the electrolytic solution so that when the object is removed from the holding means, it cannot become recontaminated by contact with the holding means.

When the holding means is a closed, or partially closed, container it is necessary that an aperture be provided such that the solution from the area surrounding the container can enter into the interior of the container, thereby establishing electrolytic contact between the portion of the solution surrounding the container, in contact with the electrodes, and the portion of the solution in which the object being disinfected is submerged.

The containers can be formed from a plurality of sections which may be joined by clamps or other fastening means, and any, or all, of the sections may be electrically conductive. The sections themselves function as the bipolar electrodes. If it is intended to provide for more than one bipolar electrode in a system, each one must be electrically insulated from the other. Thus, if a plurality of sections forming a container is provided, each section must be electrically insulated one from the other, although each would, of course, be in mutual electrolytic contact. When more than one bipolar electrode is provided, then the effect would be as if there were n+1 voltage cells in series, wherein n is the number of bipolar electrodes.

The container used as the holding means may be especially adapted to hold a particular object to be treated. For instance, if the object to be treated is an optical contact lens, such as a soft contact lens, the container should be specifically designed to accommodate the lens. In one embodiment of this invention, the container is formed of male and female members wherein the male member can be screwed, snapped, hinged or latched into the female member. The male member would have a convex section which will protrude into the female member. The female member would have a concave section which approximates the contour of the male protrusion and also of the contact lens. A lens is positioned between the concave and convex portions. It is also entirely possible to use just one member of the male-female combination to act as a suitable container. For instance, a contact lens could be placed on the convex section of the male member, which of course must be of a conductive material so that the male member functions as a bipolar electrode, and then the member with the lens can be placed in the electrolytic solution within the cell. The use of a single member has the advantage that fewer electrolytic shadows would exist about the lens and container so that more rapid and thorough disinfection of the lens and container can be achieved.

One member or both, or a portion of either member, may be formed of electrically conductive material so as to transform the container per se into one or more bipolar electrodes.

Although the use of a single pair of multiple pairs of electrodes in an electrolytic cell can work very well to disinfect an aqueous solution, if the container is of substantial size, it can take a relatively long period of time to completely disinfect the solution. Moreover, when a non-conductive object is to be disinfected, the object itself can mask portions of the solution from exposure to the electrodes. Thus, electrolytic shadows from the object can leave pockets of untreated solution which would be available to recontaminate the object being treated. Difficulty is particularly prevalent if the object being disinfected must be held in the solution in a closed or partially closed container. For instance, for obvious reasons, a contact lens cannot be simply immersed in a cell. The lens must be held in at least a partially closed container. This increases the masking or shadow effect.

The use of a bipolar electrode, thus, has a dual effect in enhancing the ability of the cell to disinfect. The bipolar electrode intensifies the field set up in the cell by the alternating current, and the bipolar electrode permits a reduction in masking. If the bipolar electrode is in electrolytic contact with the interior of the container, the portion of the solution within the container will be more rapidly and completely disinfected. Without a bipolar electrode, it would be necessary to have a recirculation device to reciruclate the electrolyte solution into and out of the container to assure complete disinfection. Using a bipolar electrode, however, the contents of the container will be disinfected so that no or very little recirculation is needed. The total time to disinfect the solution is considerably smaller than if only electrolytic electrodes alone are used. Of course, if one wanted to have a recirculating means additionally present, it would certainly further be expected to speed up disinfection time.

One could achieve similar effects, of course, by reducing the size of the electrolytic cell so as to only approximate the size of the object to be disinfected. The difficulty with such a technique, however, is that it becomes necessary to have electrical leads attached to the electrodes. In the contact lens example, which was alluded to above for illustration, if the lens container itself were made into the electrolytic cell, the electrical leads would have to be attached to the container. This becomes awkward for the user because it then becomes necessary to attach and detach leads to the container. Moreover, and probably more importantly, the outer portions of the container itself would not be disinfected. When the user would remove the contact lens from the container, the fingers would come into contact with the outer surfaces of the contaminated container. In contrast, by using the present invention the contact lens case is also disinfected and thus the problem of recontamination is minimized.

Another advantage of the use of the bipolar container concept for contact lens disinfection lies in the fact that the contact lens holding means can function both as a chamber for disinfection of the lens and as a means for disinfection of the lens holder itself.

Pathogenic micro- and macroorganisms which can be destroyed by the electrolytic treatment of the present invention include bacteria, viruses, disease flukes, protozoa, endoparasites, fungi, nematodes, algae and fungi spores.

Objects which can be disinfected by the technique of the present invention are of two basic types, one of which are those objects fabricated from non-conductive materials or essentially non-conductive materials. Thus, objects such as contact lenses, false teeth, and various beauty devices such as combs and brushes and the like can be disinfected by associating at least one bipolar electrode to the object per se or with a case which contains the object to be disinfected. Some objects such as false teeth are truly non-conducting. However, some non-conductors such as soft contact lenses are porous and therefore allow ionic conduction therethrough. Those non-conductors which possess ionic conduction properties can be disinfected at a faster rate than the true insulator objects because current ions are probably more rapidly transported through the ionic conductor. Because neither of the two classes of non-conductors can short out the electrolytic cell, special precautions are not necessary to position the objects to avoid this event.

The second type of object which can be disinfected includes those objects which are fabricated of conductive materials. Thus, objects such as various dental instruments, which are generally fabricated from steel, are conductive objects. When this type of object is disinfected by the technique of the present invention, it must be positioned within the cell such that it cannot short out the cell. In fact, if the conductive object is positioned in the correct orientation within the cell, the object itself will become a bipolar electrode when subjected to a current.

One material useful for forming the bipolar electrode of the present invention is a conducting fiber-polymer composite, particularly a composite of polymer and carbon as disclosed in copending application, Ser. No. 935,155, filed Aug. 21, 1978. Other suitable bipolar electrode materials include graphite, carbon, stable metals, the noble metals, or conductive metal oxides.

The aqueous electrolyte containing solution must be conducting and therefore should contain a salt such as an alkali metal halide or phosphate. A preferred electrolyte is an aqueous physiological saline solution.

The design of the electrolytic treatment cell which holds electrolyte solution as well as the electrodes of the cell is not critical. The cell must be large enough to hold the object to be disinfected as well as the electrolyte solution. The walls of the container of the cell can be made of any non-conducting material such as glass or any suitable type of plastic material. The cell can be designed such that the electrodes across which the electrolyzing potential is impressed are merely immersed in the electrolyte solution. Alternatively, two opposing walls of the cell or portions of the walls can themselves be the electrodes for the cell while the remaining walls of the cell which complete the enclosure are formed of a non-conductive material. In still another configuration of the cell the electrodes can be formed by depositing a metal in certain areas on the interior surfaces of the cell by vapor deposition technique to form the two electrodes for the cell. The cell is completed by attaching conductive leads to the electrodes and connecting them to a power source.

One of the interesting aspects of a bipolar electrode assembly, as in the present invention, is the ability to form-fit the object being disinfected.

The power source can be integral with the treatment cell or can be attached by any convenient pressure interlocking system to the treatment cell. In a preferred embodiment, the power supply can be programmed to operate for a sufficient period of time to ensure disinfection of the object to be sterilized. The power supply may also be equipped with a switch and indicator device which shows that the system is operational and operating during use.

Disinfection time, of course, will depend on the size of the system, power input and degree of disinfection required. For contact lenses, in a cell as described herein, suitable sterilization seems to occur within a period of less than $\frac{1}{2}$ hour. In fact, reasonably good disinfection occurs in seconds. Thus, this concept has superiorities in time as compared with presently commercial contact lens cleaning systems. Moreover, the heat generated by this system is negligible so that no damage is done to soft contact lenses, as often occurs with the currently commercially used heat boiling system.

Reference is now made to the attached drawings which describe a preferred embodiment of the device of the present invention so that a more complete appreciation of the entire invention can be achieved.

FIGS. 1–4 show various views of portions of a lens holder for soft contact lenses as well as a complete view of an integrated lens holder. FIG. 1 shows the female portion 1 of a lens holder wherein container 3 having recessed concave portions 5 is fabricated of a conductive material so that the container 3, besides acting as a lens holder, also functions as a bipolar electrode. Of course, it is most advantageous if container 3 is fabricated as a single integrated structure. Spacer pieces 7 are provided in the indicated portions of female member 1 to separate mating male member 11 shown in FIG. 2 from female member 1 to a close tolerance when the two units are united. Spacer pieces 7 are fabricated of an insulating material.

Figure 2:
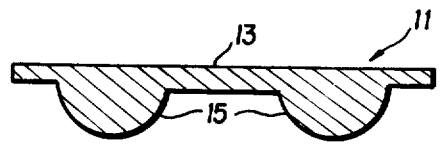
FIG. 2 is a lateral view of the male portion of a contact lens holder.

FIG. 2 shows male member 11 which consists of substrate 13 which is formed of a conductive material such as is used to fabricate female member 3 described above and convex male member 15. The material used should be compatible with soft contact lenses since members 15 can come into contact with the contact lenses. When the male member 11 is mated with female member 1, a space 17 exists between the members 15 and recessed portions 5 to receive contact lenses. The mated assembly (FIG. 4) is open to its environment when immersed in an electrolytic treatment cell for disinfection of the lenses through area 19. The electrodes of choice when contact lenses are sterilized is a physiological saline solution, although other aqueous electrolyte solutions, not detrimental to the lenses or the eye may alternatively be used.

The means by which male member 11 is mated with female member 1 is not critical and any conventional means of mating the portions of the lens holder can be employed. Thus, spacer pieces 7 can be designed such that they form a hinge-latch arrangement. In another embodiment of attachment, spacer pieces 7 can be provided with small recessed areas capable of being mated with compatible male protrusions which extend from portion 13 so that the complete device can be secured in a snap-lock arrangement.

Figure 3:
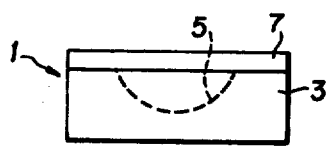
FIG. 3 is an end view of the female portion of a contact lens holder.
Figure 4:
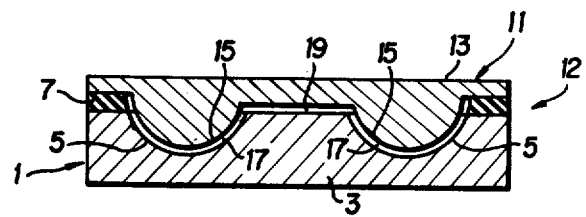
FIG. 4 is a view of the united male and female portions of a contact lens holder.

FIG. 3 shows an end view of female member 1.

Figure 5:
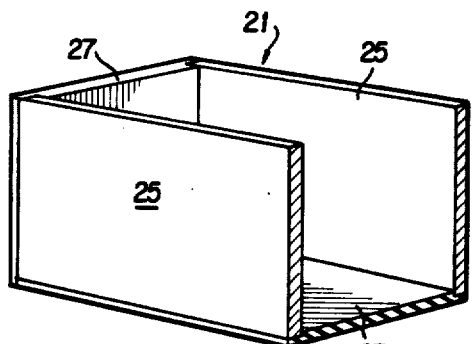
FIG. 5 is a perspective view of an electrolytic treatment cell.
Figure 7:
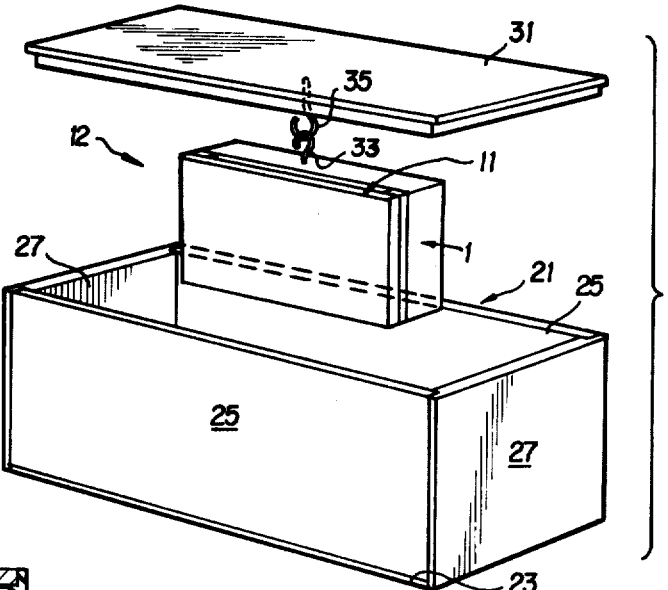
FIG. 7 is a view of a contact lens holder attached to the lid of an electrolytic treatment cell.
Figure 6:
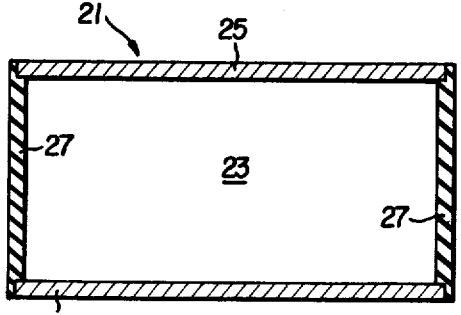
FIG. 6 is a top view of an electrolytic treatment cell.

FIG. 5 shows an embodiment of an electrolytic treatment cell 21 whose base 23 and two opposing walls 27 are formed of a non-conductive material such as glass or the like. The two remaining walls 25 of the cell, which are insulated from each other by the non-conductive walls and base, are the electrodes of the cell and are formed of an electro-conductive material. FIG. 6 shows a top view of the electrolytic cell 21 wherein walls 27 which are non-conductive complete the cell enclosure. The cell as depicted in FIGS. 5 and 6 is designed to be of such a length and depth that when a lens holder 12 containing a pair of lenses to be disinfected is immersed in the electrolyte solution in the cell, the lens holder 12 is oriented in a specific direction within the cell such that the bipolar electrode(s) are oriented in the desired manner with respect to cell electrodes 25. Of course, it is entirely possible to employ other means for placing and holding the lens holder 12 within the cell in a proper position such as by attaching the lens holder to a rigid or fixed support by means of a device on the lens holder which allows attachment to the rigid support. The electrolytic treatment cell 21 can be provided with a lid arrangement in order to prevent spillage of the electrolyte from the cell and to keep undesirable foreign matter out of the cell. In a preferred embodiment of the lid apparatus of the present invention as shown in FIG. 7, lens holder 12 can be attached to the lid 31 of the cell by suitable means 33 and 35 of attachment on the holder and lid respectively so that when the lid is placed in position over the cell, the lens holder is simultaneously lowered in position into the electrolyte in the cell.

While the foregoing discussion in combination with FIGS. 1–7 has been presented in terms of the electrolytic disinfection of contact lenses which are used to correct vision handicaps, it is equally apparent that other non-conducting objects can be disinfected in the same manner. Thus, for instance, false teeth or denture plates can be placed in a holder designed to accept the false teeth or denture. The holder can be fabricated of materials such that at least one portion of the holder also functions as a bipolar electrode when the holder is immersed in the electrolytic solution in the cell. For the disinfection of false teeth and the like there would be no particular advantage to using a physiological saline solution so that any convenient electrolyte solution could be used.

While the present invention has thus far been described in terms of fabricating a device for an object(s) to be disinfected of a material which constitutes a bipolar electrode, it will be appreciated that in other embodiments of the invention a bipolar electrode in the shape of a strip, for instance, can be attached by any suitable attachment means such as a clip to the object desired to be disinfected. Thus, an object such as a comb could be attached to a bipolar electrode and the united objects could then be lowered into a cell for disinfection.

Having generally described this invention, a further understanding can be obtained by reference to certain specific examples which are provided herein for purposes of illustration only and are not intended to be limiting unless otherwise specified.

EXAMPLE 1

An electrochemical cell was constructed in which the electrodes were formed of bulk graphite. A nonconducting support upon which was placed a single contact lens was immersed in the cell which contained a normal physiological saline solution. A current of a 25 mA/cm$^2$ current density and a voltage of 6 volts was impressed across the pair of electrodes. After 3 minutes of treatment, the initial population of Pseudomonas organisms at a concentration of $\geq 10^6$ micoorganisms/ml was reduced to zero microorganisms/ml (plate count). Repetitions of this experiment many times both with and without a contact lens in place yielded identical results.

EXAMPLE 2

Two different electrochemical cells were tested for their ability to disinfect twin contact lenses which were supported between two mating conducting supports for the lenses thereby resulting in a cell which contained two bipolar electrodes. The pertinent data for the two tests are as follows:

| Electrode Material | Bulk Graphite | Composite |
|---|---|---|
| Treatment Solution | Normal Saline | Normal Saline |
| Voltage | 10.5 V. | 6 V |
| Current Density (A.C.) | 30 mA/cm$^2$ | 12 mA/cm$^2$ |
| Initial org. population (plate count) | $10^5 \frac{\text{Pseudomonas}}{\text{ml}}$ | $10^5 \frac{\text{Pseudomonas}}{\text{ml}}$ |
| After 3 min. (plate count) | — | 0 |
| After 5 min. (plate count) | 0 | — |

Identical results were obtained multiple times in both treatment cells both with and without contact lenses in place.

The fiber composite electrodes employed above in Example 2 were composite electrodes containing conducting graphite fibers. Generally, when bulk graphite electrodes were used, good disinfection was obtained at current densities $\geq 20$ mA/cm$^2$ with cell voltages of $\geq 2$V. However, when the graphite fiber-polymer composite electrode is used, good disinfection can be achieved at current densities as low as 4 mA/cm$^2$ with cell voltages of about 2 volts. Thus, when fiber composite electrodes are used in the electrochemical disinfection of various devices, there is a significant gain in energy efficiency of the cell.

Having now fully described this invention, it will be apparent to one of ordinary skill in the art that many changes and modifications can be made thereto without departing from the spirit or scope of the invention as set forth herein.

What is claimed as new and intended to be secured by Letters Patent of the United States is:

1. A method for disinfecting an object which comprises:
   holding said object by an electrically conductive substrate,
   immersing the combination of said object and said electrically conductive substrate in an electrolyte solution within an electrolytic cell, wherein said cell contains at least one pair of electrodes,
   impressing an alternating potential across the electrodes of said cell sufficient such that said electrically conductive substrate becomes a bipolar electrode, and maintaining said bipolarism for a time sufficient to disinfect said object.

2. The method of claim 1, wherein said electrically conductive substrate comprises an electrically conductive member having a holding means to hold said object to be disinfected.

3. The method of claim 2, wherein said holding means comprises walls defining a container sufficient to receive said object to be disinfected in the interior thereof and having an electrically conductive member in electrolytic contact with the interior of said container and wherein said container will receive solution from said cell when said container is immersed in said cell.

4. The method of claim 3, wherein said container is in the form of a holder which is adapted to hold a contact lens.

5. The method of claim 4, wherein said container is formed of a male member and a female member wherein the contact lens may be positioned between said members, and wherein said male member is inserted into the female member to form said container, and wherein at least a portion of either of said members is electrically conductive.

6. The method of claim 5, wherein at least a portion of both said male and female members are electrically conductive, and wherein said electrically conductive portion of said male member is electrically insulated from the electrically conductive portion of said female member, and wherein the electrically conductive portions in both members become bipolar in use.

7. The method of claim 1, wherein said electrolyte solution is a physiological salt solution or an aqueous salt solution.

8. The method of claim 7, wherein said electrolyte solution is a physiological saline solution.

9. The method of claim 6, wherein a contact lens is placed in the container defined by said male and female members and said container is immersed into said cell wherein solution from the cell enters said container to essentially surround said lens, and wherein said solution is in electrolytic contact with the solution outside the container which is in contact with both of said electrodes.

10. An apparatus for electrolytically disinfecting an object which comprises:
   an electrolytic cell containing at least one pair of electrodes, said electrodes being positioned within said cell such that when said cell receives an electrolyte containing solution therein, said electrodes will be at least partially immersed in said solution; and
   means for holding said object to be disinfected comprising a plurality of sections, which can be joined to form walls defining a container sufficient to receive said object to be disinfected and a portion of said electrolyte containing solution in the interior of said container, at least wherein a portion of at least one of said plurality of sections is formed of an electrically conductive material which functions as a bipolar electrode when a potential is impressed across said electrodes; and
   wherein said container is of sufficient size so as to be capable of being immersed into said electrolyte containing solution, when said cell receives said electrolyte containing solution, between said electrodes; is capable of holding said object to be disinfected completely submerged in said electrolyte containing solution and permitting said electrolyte containing solution to surround said container between the walls thereof and each electrode; and has an aperture sufficient that said surrounding electrolyte containing solution is in electrolytic contact with the electrolyte containing solution within said container;

and wherein said electrically conductive material is in electrolytic contact with the contents of said container when said container is immersed in said electrolyte containing solution.

11. The apparatus of claim 10, wherein said walls comprise two sections which when joined form said container.

12. The apparatus of claim 11, wherein each of said sections is formed of an electrically conductive material to form a pair of bipolar electrodes.

13. The apparatus of claim 10, wherein a plurality of sections are formed of electrically conductive material and are in electrolytic contact with the interior of said container such that when a potential is impressed across said electrode, said plurality of sections function as a plurality of bipolar electrodes.

14. The apparatus of claim 11 which is particularly adapted for use in disinfecting contact lenses, wherein one of said sections is a male member and one of said sections is a female member and wherein a contact lens may be positioned between said male and female members such that when said male member is fitted into said female member, said contact lens is situated within said container.

15. The apparatus of claim 14, wherein at least a portion of each of said male members and said female members is formed of an electrically conductive material so as to function as a bipolar electrode when the apparatus is in use, and wherein the electrically conductive portion of said male member is insulated from the electrically conductive portion of said female member.

16. The apparatus of claim 10, wherein means are provided to hold said electrically conductive material in orientation with said electrodes such that a maximum equal and homogeneous potential drop across said electrode is attained when said material functions as a bipolar electrode.

17. The apparatus of claim 14, wherein said female member contains a recessed concave area for receiving a contact lens and said male member contains a protruding convex portion such that when said male member is inserted into said female member, said convex portion fits into said concave area thereby facilitating the holding of said lens.

18. The apparatus of claim 17, wherein an insulating spacer means for preventing physical contact between said male and female portions and to permit solution to enter the container formed by the union of said male and female portion is interposed between said male and female portions.

19. The apparatus of claim 18, wherein said spacer means provides a means for fixedly attaching said male member to said female portion by providing a hinge at one point between said male and female members and a latch arrangement at another point between said male and female members.

20. The apparatus of claim 18, wherein said spacer means is attached to one of said male and female members and is provided with at least two recessed areas for accepting mating protrusions on the member not containing the spacer means in a snap-lock arrangement when said members are united.

21. The apparatus of claim 18, wherein said spacer means is attached to one of said male and female portions and is provided with at least two protrusions which unite with mating recessed areas on the portion not containing said spacer means in a snap-lock arrangement when said portions are united.

22. The apparatus of claim 10 which further comprises:

means for positioning said holding means in said electrolyte solution to prevent contact of said bipolar electrode with said electrodes and to maintain said bipolar electrode in a proper orientation relative to said electrodes in order to subject said holding means to a continuous and homogeneous electric field.

23. The apparatus of claim 10 wherein said electrically conductive material is selected from the group consisting of carbon, graphite, graphite fiber-polymer composite and noble metals.

24. The apparatus of claim 10, wherein said object to be disinfected is a soft contact lens.

25. The apparatus of claim 10, wherein said object to be disinfected is a denture.

26. An apparatus for electrolytically disinfecting an object which comprises:

an electrolytic cell containing at least one pair of electrodes, said electrodes being positioned within said cell such that when said cell receives an electrolyte containing solution therein, said electrodes will be at least partially immersed in said solution; and a plurality of electrically conductive substrate having means for holding said object to be disinfected upon each of which an object to be disinfected may be supported, said electrically conductive substrate being of sufficient size so as to be capable of being immersed into the solution, when said cell receives said solution, between said electrodes, such that the electrolyte completely surrounds said holding means and said object; and wherein said substrate functions as bipolar electrodes when a potential is impressed across said electrodes.

* * * * *